(12) United States Patent
Weber et al.

(10) Patent No.: US 7,854,714 B1
(45) Date of Patent: Dec. 21, 2010

(54) THUMB WRAP

(75) Inventors: James J. Weber, Santa Barbara, CA (US); David Auerbach, Calabasas, CA (US)

(73) Assignee: Weber Orthopedic Inc., Santa Paula, CA (US)

( * ) Notice: Subject to any disclaimer, the term of this patent is extended or adjusted under 35 U.S.C. 154(b) by 28 days.

(21) Appl. No.: 11/807,378

(22) Filed: May 29, 2007

(51) Int. Cl.
- *A61F 5/00* (2006.01)
- *A61F 13/06* (2006.01)
- *A61F 5/37* (2006.01)
- *A61B 19/00* (2006.01)

(52) U.S. Cl. ............... 602/22; 602/5; 602/20; 602/21; 602/60; 602/61; 602/62; 128/846; 128/869; 128/878; 128/879; 128/880

(58) Field of Classification Search ............ 602/5, 602/20–22, 60–62; 128/878–880, 898
See application file for complete search history.

(56) References Cited

U.S. PATENT DOCUMENTS

| 4,287,609 | A | * | 9/1981 | Amadeo | 2/16 |
|---|---|---|---|---|---|
| D287,640 | S | * | 1/1987 | Primiano | D24/190 |
| D373,639 | S | * | 9/1996 | McKie | D24/190 |
| 6,702,772 | B1 | | 3/2004 | Goldtiz | |
| 6,955,484 | B2 | * | 10/2005 | Woodman | 396/423 |

* cited by examiner

*Primary Examiner*—Patricia M Bianco
*Assistant Examiner*—Brandon Jackson
(74) *Attorney, Agent, or Firm*—William W. Haefliger

(57) ABSTRACT

In a thumb wrap, the combination comprising a user's hand and wrist flexible wrap, a generally tubular portion to receive the user's thumb, said tubular portion being integral with the hand and wrap, a securing strap endwise seamlessly integral with the hand and wrist wrap, and extending with elongation to be wrapped over the hand and wrist wrap palmwise and endwise of the tubular portion and then to be wrapped between the user's thumb and forefinger, and then back over the hand and wrist wrap for tensioned tightening and for the effecting thumb positively supported securement.

8 Claims, 5 Drawing Sheets

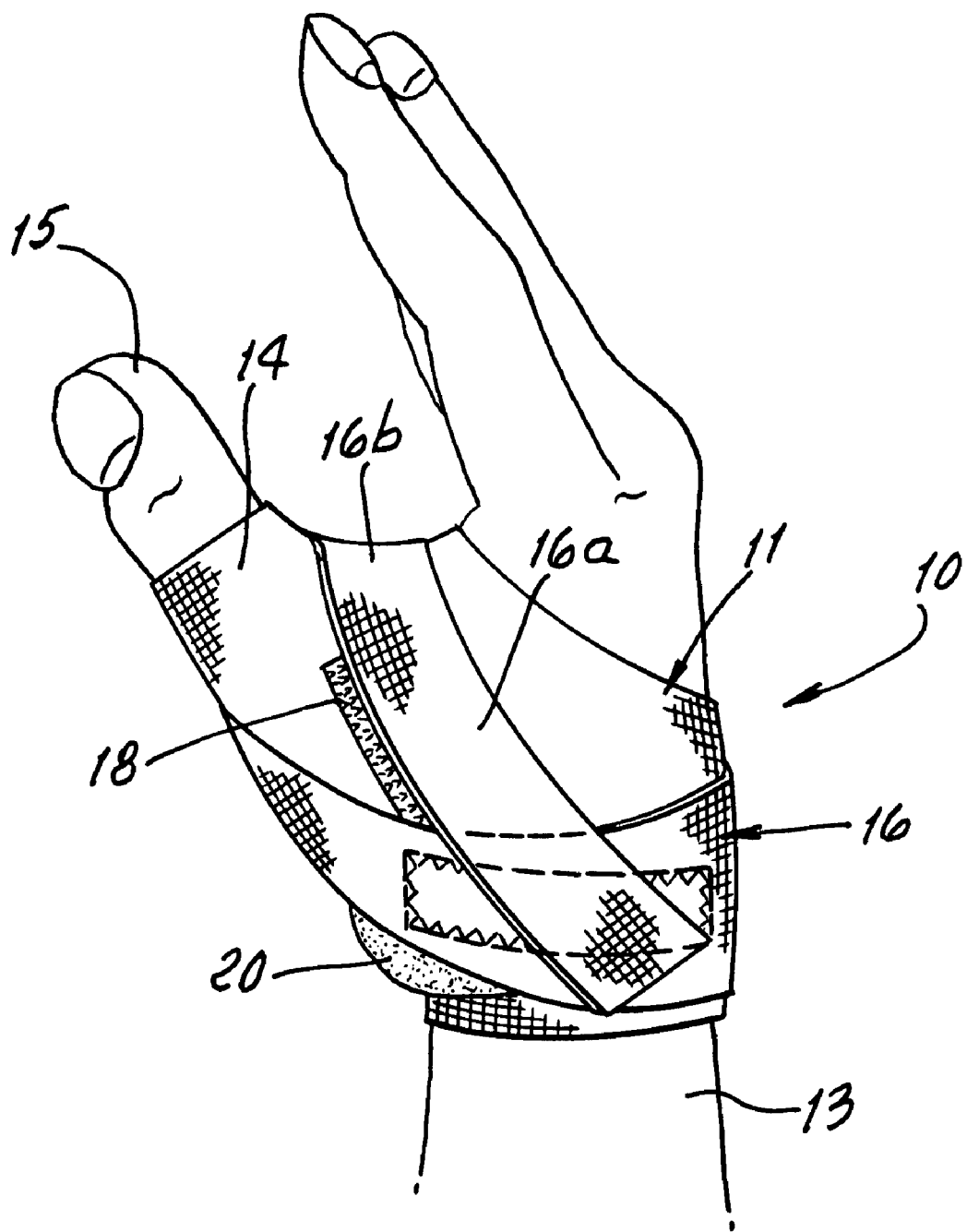

THUMB WRAP

BACKGROUND OF THE INVENTION

This invention relates generally to a brace or thumb wrap operable to support the thumb of the user; and more particularly concerns a brace applicable to the wrist of the user or wearer, for enabling a tightening strap or straps to be easily wrapped relative to the thumb, tensioned and secured.

Prior braces lacked the unusually advantageous combinations of features referred to, as well as the wide ranges of fit and adjustability, both about the wrist and also in supporting relation to the wearer's thumb, as are disclosed herein. There is need for the multiple interrelated improvements as are now afforded by the present invention.

SUMMARY OF THE INVENTION

It is a major object of the invention to provide an improve thumb wrap construction and configuration, meeting the above needs. Basically, the improved device comprises:

a) a user's hand and wrist flexible wrap, b) a generally tubular portion to receive the user's thumb, that tubular portion being integral with the hand and wrist wrap, c) a securing strap endwise seamlessly integral with the hand and wrist wrap, and extending with elongation to be wrapped over the hand and wrist wrap palmwise and endwise of the tubular portion and then to be wrapped between the user's thumb and forefinger, and then back over the hand and wrist wrap for tensioned tightening and for effecting positive support, whereby main extent of the thumb is effectively supported.

Another object includes provision of a grip positioned on the wrap to be pulled, to enhance said tightened securement of the strap, by tightened securement of the wrap, the strap formed as an extension of the wrap, whereby pulling of the grip tensions the strap and the wrap at the time of application. Typically the grip has flexible loop configuration, and is located at the underside of the strap to be held down by the tightened and secured strap. Also, the grip may have hook and pile attachment to the strap.

A further object includes provision of said tubular portion to have a terminal edge extent free of reinforcement, to enable selected severing for selected thumb exposure beyond the tubular portion.

Yet another object is to provide the securing strap with releasable hook and pile attachment to the hand and wrist flexible wrap palmwise of said tubular portion.

An additional object includes securing the tightening strap in position, by:

i) pulling the grip loop in a direction to enable tensioned urging of the strap against the web between the user's thumb and forefinger, ii) simultaneously urging the strap endwise and clamping the strap over and against the hand backside for fixing said tightened securement.

These and other objects and advantages of the invention, as well as the details of an illustrative embodiment, will be more fully understood from the following specification and drawings, in which:

DRAWING DESCRIPTION

FIG. 5 is a view taken on lines 5-5 of FIG. 4.

DRAWING DESCRIPTION

Figure 1:
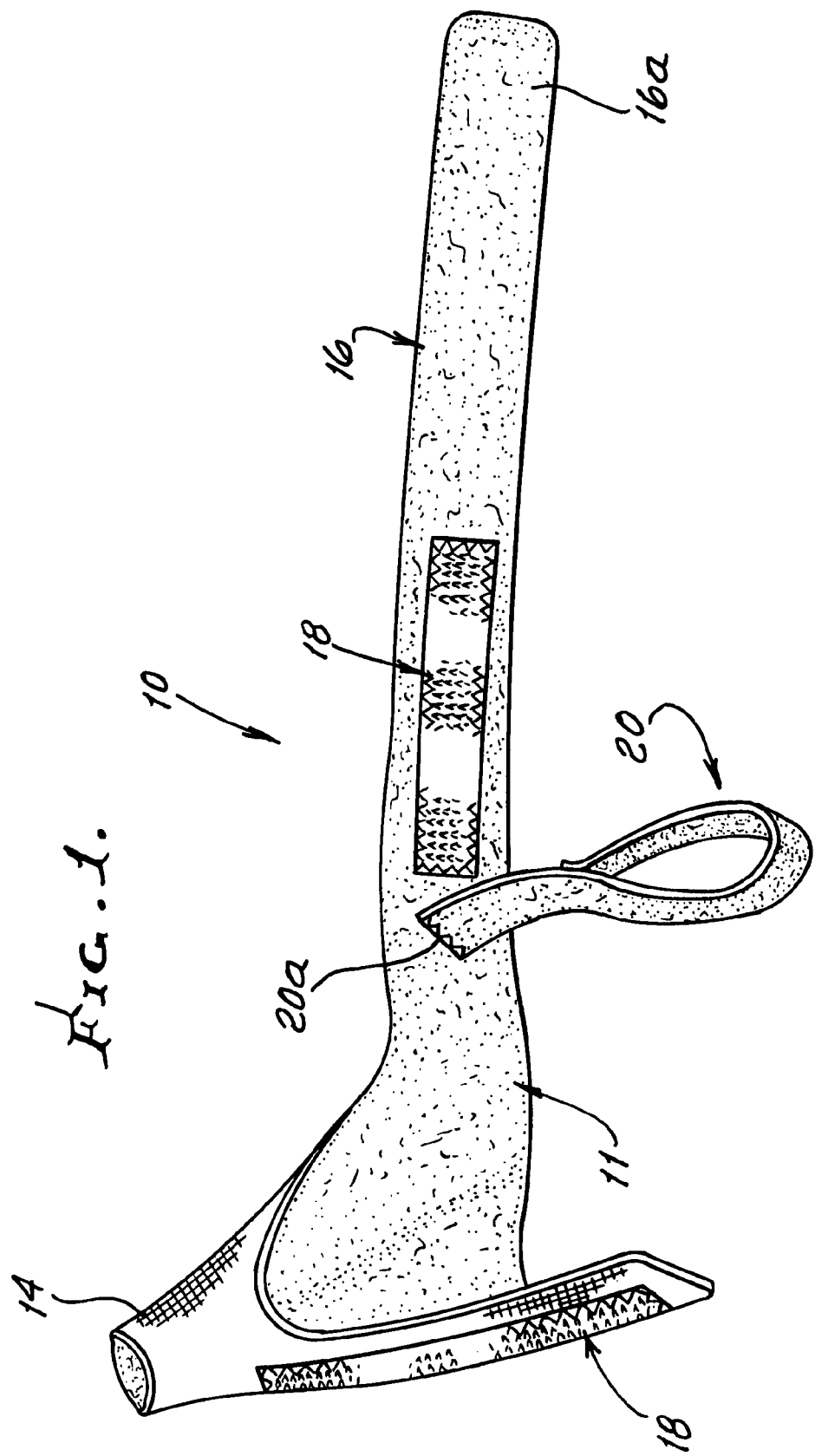
FIG. 1 is a top edge view of a preferred thumb wrap embodying the invention.
Figure 2:
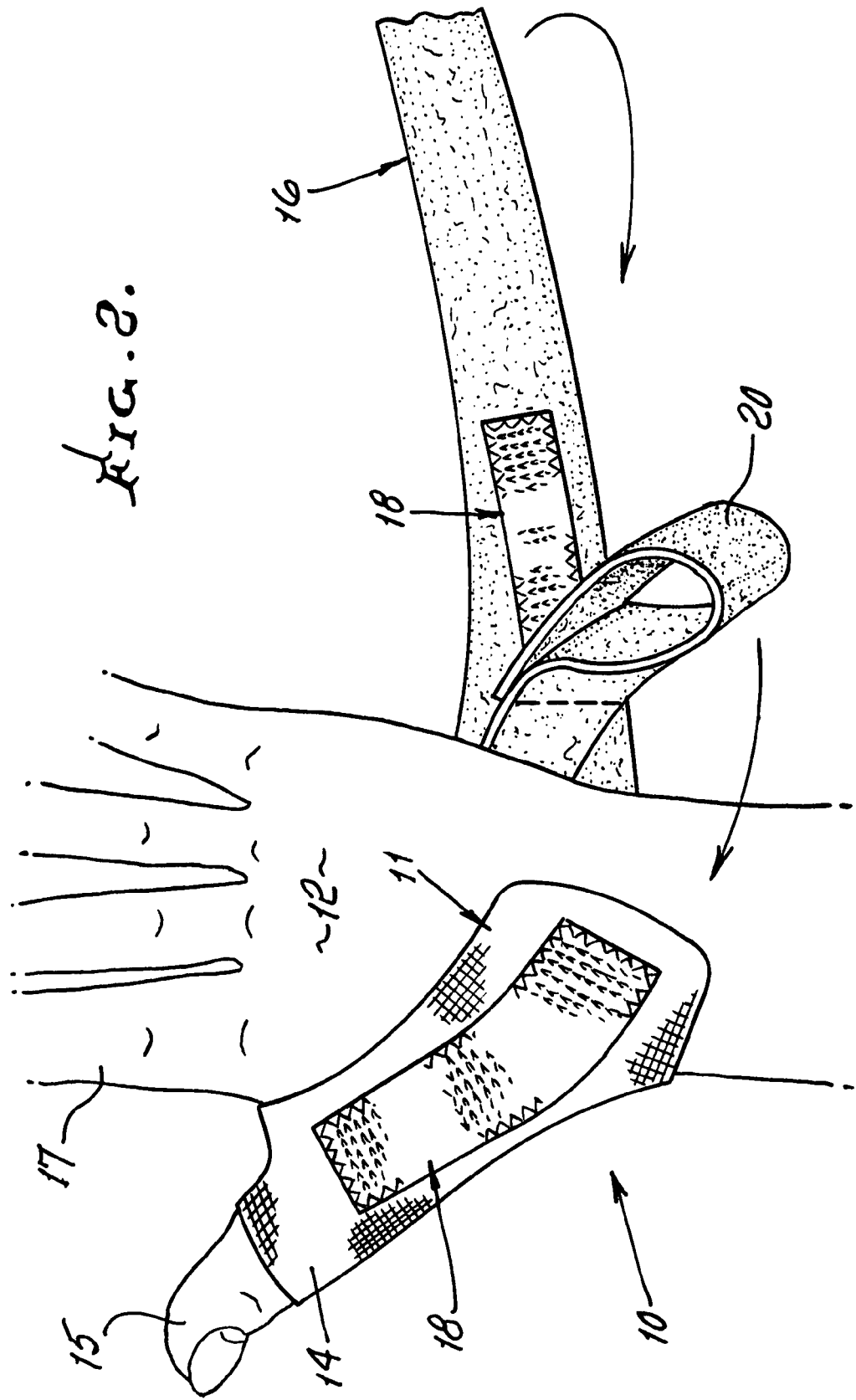
FIG. 2 is an elevation showing the FIG. 1 thumb wrap partially applied to the thumb, and left hand of a user, or palm side.

Referring first to FIGS. 1 and 2 they show a thumb wrap 10, that basically comprises:

a) a one-piece flexible wrap 11 for application to a user's hand 12 and wrist 13;

b) a generally tubular portion 14 of the wrap to receive the user's thumb 15 (see FIGS. 2-5), that tubular portion being integral with the hand and wrist wrap; and c) a securing strap 16 that is endwise seamlessly integral with the wrap 11, and extending with elongation as at 16*a* to a wrapped over the hand and wrist wrap (at 16*a* in FIG. 4) palmwise and endwise of the tubular portion, and then to be wrapped (as at 16*b* in FIGS. 4-6) between the user's thumb 15 and forefinger 17, and then back over (at 16*c* in FIG. 3) the hand and wrist wrap for tensioned tightening securement, as by hook and pile connection at 18.

In accordance with one important aspect of the invention, a finger grip is positioned on or in association with the strap 11 to be pulled to enhance endwise tightening of the strap by tensioned securement to the wrap. In the drawings, the grip is, or is defined by, a flexible loop 20 of material located at the underside of the strap and connected to the strap at 20*a* to be held down, flattened against the wrap by the strap. In this regard, the strap is formed, for simplicity and effectiveness, as by a narrowed seamless extension of the wrap.

Figure 3:
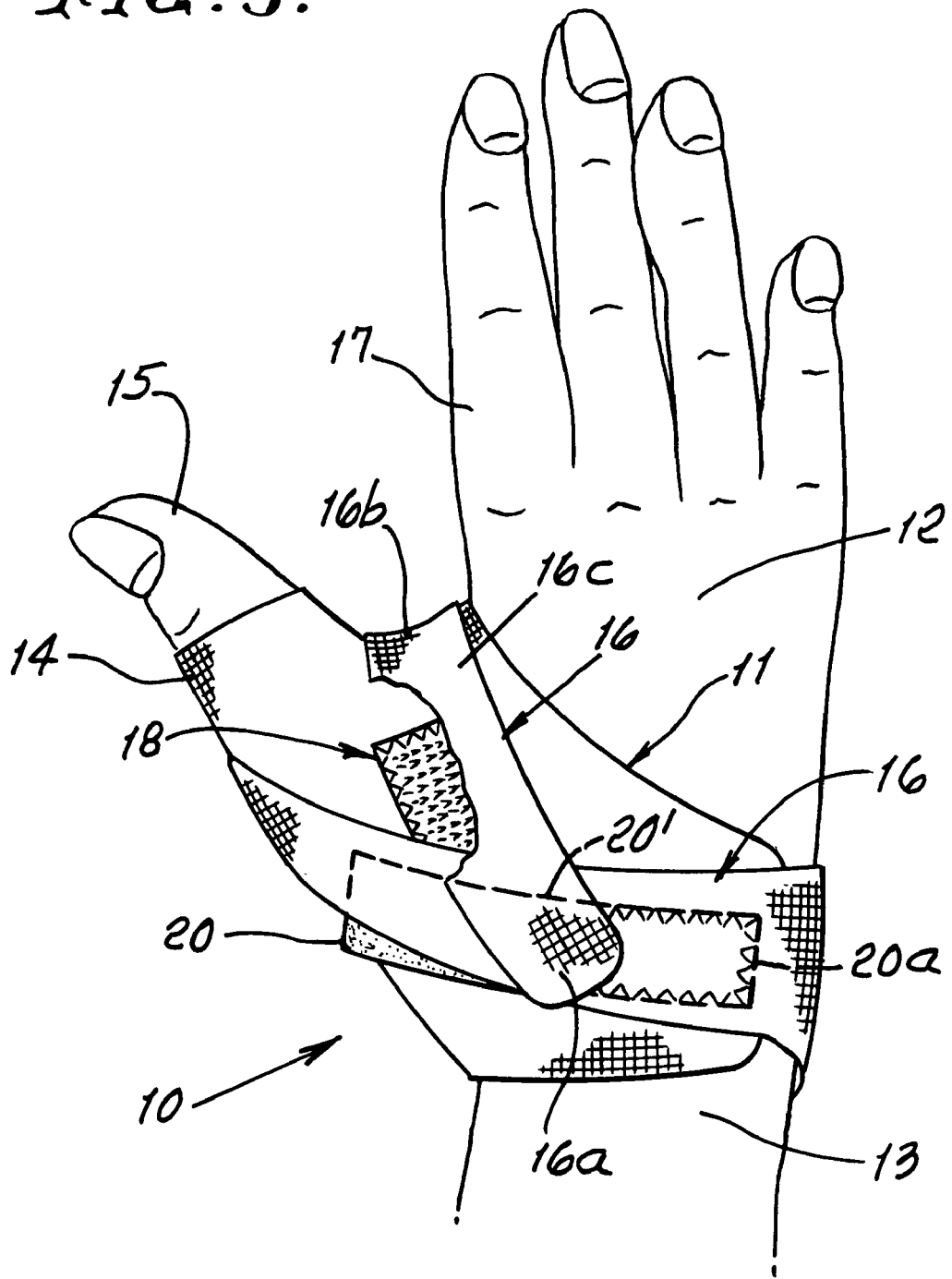
FIG. 3 is a view like FIG. 2 showing the thumb wrap fully applied to the hand of the user.
Figure 4:
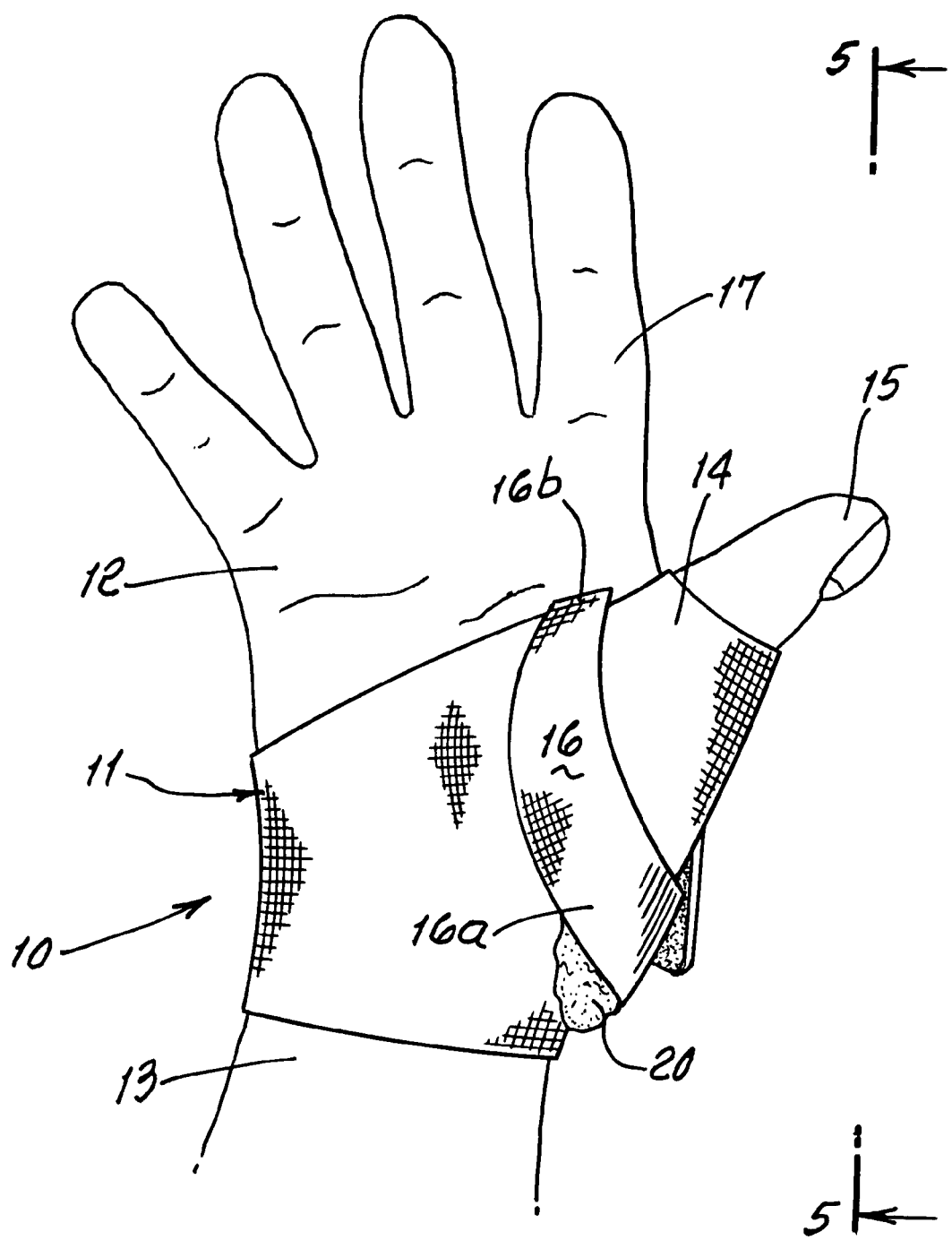
FIG. 4 is a view showing the thumb wrap fully applied to the hand, at the back side of the hand.

In applying the device to the wrist 13 or hand, the user inserts the thumb through tubular portion 14, which then serves to position part of the wrap supported about the wrist, and the user then pulls on the loop with his other hand to tension the wrap about the wrist, while then simultaneously pulling the strap endwise for wrapping it at 16*a* about a lower extension of 14, as in FIGS. 3 and 4; the user then pulls the strap over the space between the thumb and forefinger as at 16*b* in FIG. 3, and then tensions it downwardly at 16*c* for hook and pile connection at 18 to hook or pile zone 18*a* on the wrap. The wrap and strap are both thereby tensioned to positively support the thumb, within the tube 14, since the tube is supported by strap tension.

A further feature is location of the loop 20 at the underside of the strap to be held down against the wrap, as indicated by broken lines 20' in FIG. 3.

Another feature of the invention is the provision of the upper terminal edge portion 14*a* of 14 to be free of reinforcement, which enables selected severing or trimming, for desired thumb projection and exposure at 15*a*.

The method of securing the tightening trap in position includes the steps i) pulling the grip loop in a direction to enable tensioned urging of the strap against the web between the user's thumb and forefinger, ii) simultaneously urging the strap endwise and clamping the strap over and against the hand backside for fixing said tightened securement.

We claim:

1. The method of providing a secure thumb wrap, the steps including:
    a) providing a user's hand and wrist flexible wrap,
    b) providing a generally tubular portion of the wrap to receive the user's thumb, said tubular portion being integral with the hand and wrap,
    c) providing a securing strap endwise seamlessly integral with the hand and wrist wrap, and extending with elongation to be wrapped over the hand and wrist wrap, palmwise and endwise of the tubular portion, and then to be wrapped between the user's thumb and forefinger, and then back over the hand and wrist wrap for tensioned tightening and for the effecting thumb supported securement,
    d) providing a grip positioned on the wrap to be pulled to enhance said tightened securement of the strap, by tightened securement of the wrap, the strap formed as an extension of the wrap,
    e) the grip having flexible loop configuration,
    f) flattening the grip loop to hold a mid-portion thereof retained in flattened condition beneath the strap when the strap is in tightened securement, as aforesaid, pulling the strap endwise to have a terminal end portion positioned to extend sidewise crossing over said mid-portion of the flattened loop when the strap is in tightened securement, tensioning the strap to provide releasable hook and pile attachment to the hand and wrist flexible wrap palmwise of said tubular portion, and effecting hook and pile connection of the strap to the wrap along length of the terminal end portion sidewise approaching the undersides of both the loop and wrap extent supporting the loop, while the strap is pulled endwise from a region between the user's thumb and forefinger.

2. The method of claim 1 wherein the grip loop is located at the underside of the strap to be held down by the strap.

3. The method of claim 1 wherein said tubular portion is provided to have terminal edge extent free of reinforcement, to enable selected severing for selected thumb exposure endwise beyond the tubular portion.

4. The method of claim 1 wherein the grip is provided to have hook and pile attachment to the strap.

5. The method of claim 1 wherein the grip loop is provided to have releasable hook and pile attachment to the strap.

6. The method of claim 1 wherein the securing strap has is provided to have releasable hook and pile attachment to the hand and wrist flexible wrap palmwise of said tubular portion, as the strap approaches said loop mid-portion.

7. The method of claim 1 wherein the entire thumb wrap is provided to have one-piece construction.

8. The method of claim 1 wherein the grip is provided to have one-piece construction.

* * * * *